(12) United States Patent
Höfel

(10) Patent No.: US 10,954,175 B2
(45) Date of Patent: Mar. 23, 2021

(54) PROCESS AND PLANT FOR PRODUCING OLEFINS

(71) Applicant: LINDE AKTIENGESELLSCHAFT, München (DE)

(72) Inventor: Torben Höfel, Munich (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 16/488,355

(22) PCT Filed: Feb. 23, 2018

(86) PCT No.: PCT/EP2018/054518
§ 371 (c)(1),
(2) Date: Aug. 23, 2019

(87) PCT Pub. No.: WO2018/154056
PCT Pub. Date: Aug. 30, 2018

(65) Prior Publication Data
US 2020/0231522 A1    Jul. 23, 2020

(30) Foreign Application Priority Data

Feb. 24, 2017    (EP) ..................................... 17157933

(51) Int. Cl.
*C07C 5/48*    (2006.01)
*C07C 7/04*    (2006.01)
(Continued)

(52) U.S. Cl.
CPC .................. *C07C 5/48* (2013.01); *C07C 7/04* (2013.01); *C07C 7/10* (2013.01); *C07C 11/04* (2013.01)

(58) Field of Classification Search
CPC .... C07C 5/48; C07C 7/04; C07C 7/10; C07C 7/11; C07C 11/04; C07C 51/215; C07C 51/43; C07C 51/44; C07C 51/48
See application file for complete search history.

(56) References Cited

U.S. PATENT DOCUMENTS

| | | | | |
|---|---|---|---|---|
| 4,899,003 A | * | 2/1990 | Manyik | C07C 5/48 585/313 |
| 7,687,677 B1 | | 3/2010 | O'Brien et al. | |
| 2014/0249339 A1 | | 9/2014 | Simanzhenkov et al. | |

FOREIGN PATENT DOCUMENTS

| | | |
|---|---|---|
| EP | 0479692 A1 | 4/1992 |
| EP | 0694524 A1 | 1/1996 |
| WO | WO 2015059275 A1 | 4/2015 |

OTHER PUBLICATIONS

PCT/EP2018/054518 International Search Report and Written Opinion dated May 9, 2018, 8 pages.

* cited by examiner

*Primary Examiner* — Youngsul Jeong
*Assistant Examiner* — Jason Y Chong
(74) *Attorney, Agent, or Firm* — Lathrop GPM LLP

(57) ABSTRACT

Proposed is a process (100) for producing ethylene in which ethane in a reaction input is partly catalytically converted by oxidative dehydrogenation (1) in the presence of oxygen to obtain a gaseous first component mixture containing at least ethane, ethylene, acetic acid and water. It is provided that at least a portion of the gaseous first component mixture is subjected to a scrubbing operation with a scrubbing liquid to obtain a liquid second component mixture containing water and acetic acid, that a first proportion of the second component mixture is used for forming the scrubbing liquid, that a second proportion of the second component mixture is subjected to a solvent extraction to obtain a liquid third (Continued)

component mixture containing at least one organic solvent and acetic acid and that at least a portion of the liquid third component mixture is heated and subjected to a distillation to obtain a liquid containing predominantly or exclusively acetic acid. The heating of the third component mixture or the portion thereof subjected to the distillation is performed at least partly in heat exchange with the first component mixture and/or with the first and/or with the second proportion of the second component mixture. A corresponding plant likewise forms part of the subject matter of the present invention.

19 Claims, 1 Drawing Sheet

(51) Int. Cl.
  *C07C 7/10* (2006.01)
  *C07C 11/04* (2006.01)

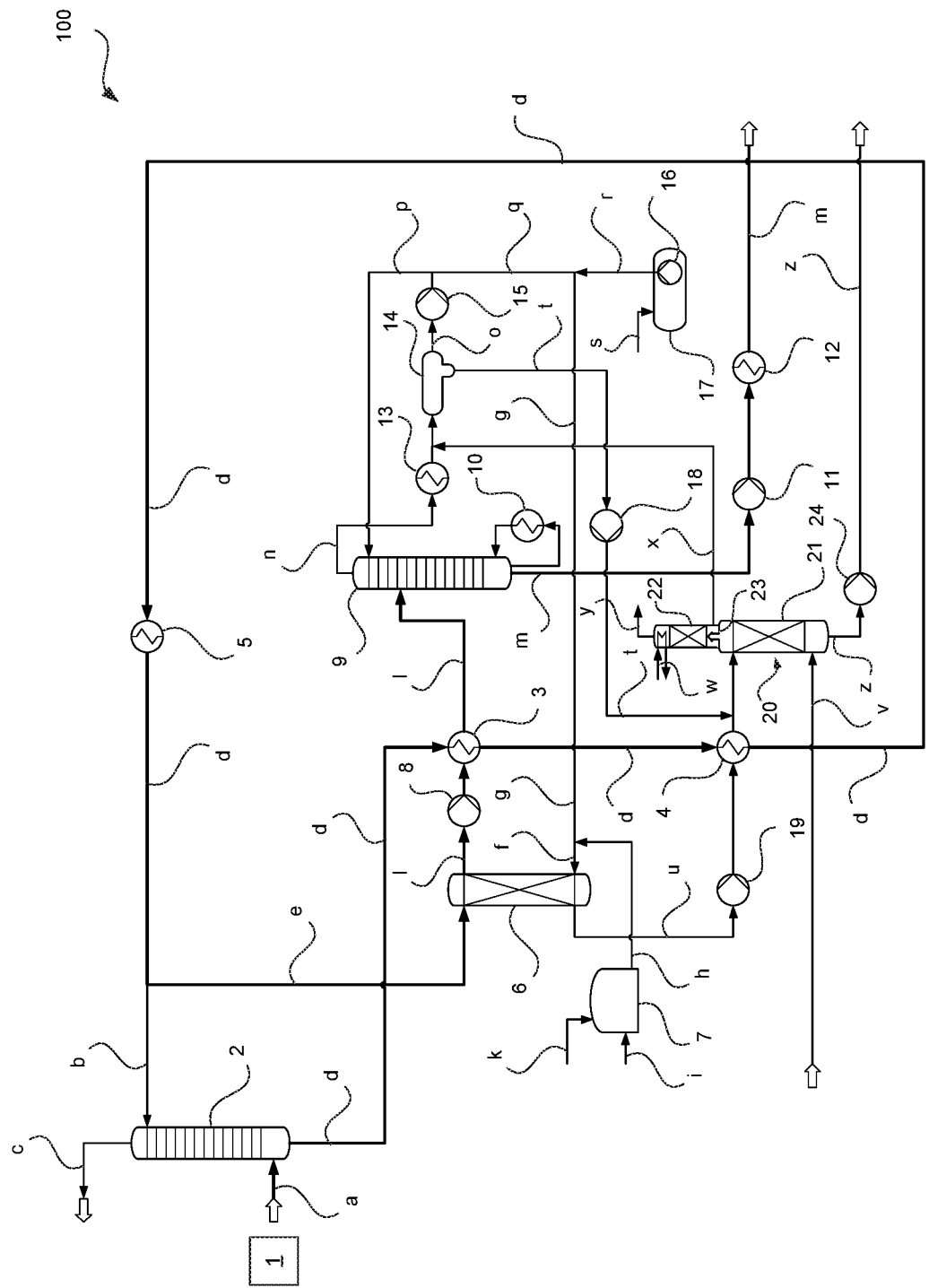

PROCESS AND PLANT FOR PRODUCING OLEFINS

The invention relates to a process for producing olefins and a corresponding plant according to the preambles of the independent claims.

PRIOR ART

Oxidative dehydrogenation (ODH) of paraffins having two to four carbon atoms is known in principle. In ODH the recited paraffins are reacted with oxygen to afford inter alia olefins of identical carbon number and water.

ODH may be advantageous compared to established processes for producing olefins such as steamcracking or catalytic dehydrogenation. For instance, there is no thermodynamic equilibrium limitation on account of the exothermicity of the reactions involved. ODH may be performed at comparatively low reaction temperatures. Regeneration of the employed catalysts is in principle not necessary since the presence of oxygen allows an in situ regeneration. Finally, compared to steamcracking, smaller amounts of worthless byproducts such as coke are formed.

For further details concerning ODH, reference is made to the relevant technical literature, for example Ivars, F. and López Nieto, J. M., Light Alkanes Oxidation: Targets Reached and Current Challenges, in: Duprez, D. and Cavani, F. (ed.), Handbook of Advanced Methods and Processes in Oxidation Catalysis: From Laboratory to Industry, London 2014: Imperial College Press, pages 767-834, or Gärtner, C. A. et al., Oxidative Dehydrogenation of Ethane: Common Principles and Mechanistic Aspects, ChemCatChem, vol. 5, no. 11, 2013, pages 3196 to 3217.

Particularly when using MoVNbTeOx catalysts under industrially relevant reaction conditions ODH forms significant amounts of the respective carboxylic acids of the employed paraffins as by-products. For economic plant operation, corresponding joint production of olefins and the corresponding carboxylic acids is generally appropriate when using the described catalyst type. This applies in particular to ODH of ethane (so-called ODH-E) in which acetic acid is simultaneously formed. The olefins and the carboxylic acids need to be separated from one another if they are to be provided separately as products.

In addition ODH forms appreciable amounts of inter alia carbon monoxide and carbon dioxide as byproducts which together with water, residual oxygen and residual ethane are likewise present in a gas mixture formed in ODH and must be removed from the respective primary products, i.e. the olefins and the corresponding carboxylic acids.

The problem addressed by the present invention is that of improving such a separation and in particular making it more efficient.

DISCLOSURE OF THE INVENTION

Against this background, the present invention proposes a process for producing olefins and a corresponding plant having the features of the independent claims. Embodiments are in each case subject matter of the dependent claims and of the description which follows.

Material streams, gas mixtures etc. may in the context of the present usage be rich or poor in one or more components, wherein the indication "rich" may represent a content of no less than 99%, 99.5%, 99.9% or 99.99% and the indication "poor" may represent a content of no more than 1%, 0.5%, 0.1% or 0.01% on a molar, weight or volume basis. If a plurality of components are reported the indication "rich" or "poor" relates to the sum of all components. If reference is made for example to "oxygen" or "ethane", a pure gas or else a mixture rich in the respective component may be concerned.

Material streams, gas mixtures etc. may in the context of the present usage also be "enriched" or "depleted" in one or more components, wherein these terms are based on a content in a starting mixture. They are "enriched" when they contain not less than 1.5 times, 2 times, 5 times, 10 times, 100 times or 1000 times the content, and "depleted" when they contain not more than 0.75 times, 0.5 times, 0.1 times, 0.01 times or 0.001 times the content, of one or more components based on the starting mixture.

The terms "pressure level" and "temperature level" are used hereinbelow to characterize pressures and temperatures, these being intended to express that pressures and temperatures need not be present in the form of exact pressure/temperature values. A pressure level or temperature level may for example be within ±1%, 5%, 10%, 20% or 50% of a mean value. A plurality of pressure and temperature levels may represent disjoint or overlapping ranges. The same pressure/temperature level may for example still be present even when pressures and temperatures have been reduced on account of transmission losses or cooling. Pressure levels reported here in bar are absolute pressures.

A "distillation column" in the context of the present usage of the term is a separating unit adapted for at least partly fractionating a substance mixture introduced in gaseous or liquid form or in the form of a biphasic mixture having liquid and gaseous proportions, optionally also in the supercritical state, by distillation/rectification, i.e. respectively generating from the substance mixture pure substances or at least substance mixtures having different compositions. Distillation columns are typically configured as cylindrical metal containers provided with internals, for example separating trays or ordered or unordered packings. A distillation column comprises a bottoms evaporator. This is a device having a heat exchanger which is heated and adapted for heating a liquid fraction accumulating in the bottom of the rectification column, also known as bottoms liquid. By means of a bottoms evaporator a portion of the bottoms product is continuously evaporated and recycled in gaseous form in the separating region.

By contrast, a "scrubber" in the context of the present usage of the term is a separating unit adapted for running a gas mixture introduced in gaseous form in countercurrent to a liquid described as a scrubbing liquid/absorption liquid to transfer components of the gas mixture from said gas mixture into the scrubbing liquid. Components transferred from the gas mixture into the scrubbing liquid may be solid, liquid or gaseous substances, in the present case in particular water and acetic acid, which are present in the gas mixture in gaseous or finely dispersed liquid form. A scrubber too may contain internals which may be configured comparably to those of a distillation column and are provided to produce the greatest possible transfer area between the gas mixture and the scrubbing liquid. However, a scrubber does not typically comprise a bottoms evaporator.

An "extraction column" in the context of the present usage of the term is a liquid-liquid extractor in which an extraction is performed in countercurrent. Different designs may be employed but all are based on a common operating principle. In particular, extraction columns may have an upright vertical configuration, wherein introduced continuously at the top is the higher specific gravity liquid (in this case the liquid mixture to be extracted) and at the bottom is the lower specific gravity liquid (in this case the extractant). To achieve the greatest possible transfer area between the liquids fine dispersion is undertaken here too. Especially suitable apparatuses and internals facilitate intensive commixing. The lower specific gravity liquid (extract-laden solvent) is withdrawn at the top of the extraction column.

For configurations and specific embodiments of such columns reference is made to textbooks (see for example K. Sattler, "Thermische Trennverfahren: Grundlagen, Auslegung, Apparate", 3rd edition, Wiley-VCH, Weinheim 2001).

As mentioned at the outset, particularly when using MoVNbTeOx catalysts ODH can form significant amounts of the respective carboxylic acids of the employed paraffins as byproducts. Further byproducts are inter alia carbon monoxide and carbon dioxide. A gas mixture withdrawn from an ODH reactor typically further contains reaction and process water, residual oxygen and residual ethane. Such a gas mixture is referred to here as "process gas" from ODH or "first component mixture". As mentioned the process gas contains one or more olefins as primary product(s) and also byproducts and unconverted reactants. In the case of ODH-E the primary products are ethylene and acetic acid.

Advantages Of The Invention

US 2014/0249339 A1 discloses subjecting a process gas of an ODH to a water scrubbing operation to cool, and to scrub water-soluble components out of, said gas (so-called water quench). The liquid generated in such a water quench is essentially an aqueous acetic acid solution having a content of typically 5-20% by weight, for example about 11% by weight, of acetic acid. The acetic acid solution is generated at a temperature of typically 75° C. to 100° C., for example about 90° C. It is also referred to hereinbelow as "second component mixture". It will be appreciated that an acetic acid solution generated in such a water quench may also contain further components, for example light hydrocarbons, which are scrubbed out to a certain extent.

To obtain the acetic acid from the acetic acid solution different processes may in principle be employed, for example conventional distillation processes, solvent extraction processes and/or processes using suitable entrainers. For energetic reasons in particular the prior art typically employs the latter processes for more dilute acetic acid solutions.

The present invention now comprises both such a water quench in which such an aqueous acetic acid solution is obtained and the use of a liquid-liquid extraction of the aqueous acetic acid solution, for example using methyl tert-butyl ether (MTBE) or ethyl acetate, followed by a solvent distillation. The aqueous acetic acid solution is initially supplied to an extraction column which is advantageously operated at atmospheric conditions (ambient pressure and ambient temperature). The acetic acid is extracted from the aqueous acetic acid solution in the extraction column using the recited solvents. The obtained solvent-acetic acid mixture is subsequently distilled in a distillation column at atmospheric conditions to obtain pure acetic acid. Generated at the bottom of this distillation column is substantially pure acetic acid and obtained at the top is a component mixture which is also referred to hereinbelow as "fourth" component mixture and contains the acetic acid not transferred into the bottom of the distillation column, small amounts of water and otherwise predominantly solvent. Before or after introduction into the distillation column the solvent-acetic acid mixture is heated. This heating is preferably to a temperature level close to the evaporation temperature of the solvent-acetic acid mixture. In this way the energy requirement for the distillation which is attributable to a substantial extent to the heat requirement of a bottoms evaporator employed in the distillation may be reduced in the context of the present invention, while simultaneously, as elucidated below, other material streams may be effectively cooled.

Overall, the present invention proposes a process for producing ethylene in which ethane in a reaction input is partly catalytically converted by oxidative dehydrogenation (ODH, ODH-E) in the presence of oxygen to obtain a gaseous first component mixture containing at least ethane, ethylene, acetic acid and water. The present invention may therefore in principle be employed in a known a process for ODH-E. For further details, reference is made to the technical literature cited at the outset. The first component mixture obtained in ODH-E may be subjected to a conditioning, for example a pre-cooling, before it is treated as described hereinbelow in the process according to the invention. The first component mixture is a product gas/process gas from ODH-E.

If it is stated that such a first component mixture contains ethane, ethylene, acetic acid and water it will be appreciated that this does not exclude the possibility that the component mixture contains further components, in particular byproducts of ODH-E or components already present in the reaction input but not converted in the ODH-E which are described here as inert components. An inert component is not necessarily a classical inert gas but also includes for example any methane present in the reaction input which undergoes little, if any, conversion in ODH-E.

The present invention provides that at least a portion of the gaseous first component mixture is subjected to a scrubbing operation with a scrubbing liquid to obtain a liquid second component mixture containing water and acetic acid. The scrubbing operation is in particular performed in a scrubber such as was elucidated hereinabove. The scrubbing operation is used not only for purification of such a first component mixture but in particular also for cooling thereof. Such a scrubbing operation is in principle known from the prior art and is also referred to as a water quench (see above).

The present invention further provides that a first proportion of the second component mixture is used for forming the scrubbing liquid and that a second proportion of the second component mixture is subjected to a solvent extraction to obtain a liquid third component mixture containing an organic solvent and acetic acid. Thus, in the context of the present invention, a circuit is formed, wherein the scrubbing liquid is always formed from the bottoms liquid of the scrubber. It is advantageous when, as also mentioned hereinbelow, the first and the second proportion of the second component mixture are cooled before their corresponding use. This represents an essential aspect of the present invention. The solvent extraction is preferably effected using an extraction column such as was elucidated at the outset.

Finally the present invention provides that at least a portion of the liquid third component mixture is heated and subjected to a distillation to obtain a liquid containing predominantly or exclusively acetic acid. This distillation is thus used to provide an acetic acid-rich product, in particular substantially pure acetic acid (glacial acetic acid). The use of the present invention makes it possible to produce such a pure product and thus fully utilize the synthesis capacity of ODH-E.

However, in the context of the present invention it was also recognized that in particular such a distillation has comparatively high energy requirements since heating media are required here which cannot be provided without additional energy requirements. In particular a distillation as may be employed in the context of the present invention is performed using a bottoms evaporator operated with low pressure steam. Such low pressure steam must be provided at great expense and the distillation is thus the main energy consumer in a separation of this type. This is likewise addressed by the invention.

According to the present invention the heating of the third component mixture or the portion thereof subjected to the distillation is performed at least partly in heat exchange with the first component mixture and/or with the first and/or with the second proportion of the second component mixture. In other words the third component mixture/the portion thereof subjected to the distillation is heated or even pre-evaporated or fully evaporated prior to performing the distillation (though as mentioned heating by means of an intermediate reboiler in the distillation is also possible). This makes it possible to perform the distillation with lower energy requirements since smaller amounts of heat and thus low pressure steam need to be provided in the bottoms evaporator of a corresponding distillation column. The heating may in particular be effected at a temperature level below the temperature level required for operation of the bottoms evaporator (40° C. to 120° C.; 120° C. is the boiling point of acetic acid and the minimum required bottoms temperature).

The heating may be performed using one or more heat exchangers through which the third component mixture is passed before introduction into the distillation column. In a further embodiment of the invention the heat input may alternatively or in addition be effected directly in the distillation by means of an intermediate reboiler which may likewise be heated in the same way. The use of an intermediate reboiler also has the effect of energy saving at the bottom of the distillation column. Thus in this case too at least a portion of the liquid third component mixture is heated and subjected to a distillation to obtain a liquid containing predominantly or exclusively acetic acid, wherein the third component mixture or the portion thereof subjected to the distillation is performed at least partly in heat exchange with the first component mixture and/or with the first and/or with the second proportion of the second component mixture. Only the heat exchange is in this case effected at another location.

A heating according to the just-now elucidated embodiment of the present invention is therefore particularly advantageous because it may be effected through heat integration wherein an in any case necessary cooling of the first component mixture and/or of the first and/or of the second proportion of the second component mixture may be undertaken.

As already mentioned hereinabove the second component mixture/the first and/or second proportion thereof is cooled before use thereof as scrubbing liquid but also before introduction thereof into the solvent extraction. The second component mixture/the first and/or second proportion thereof is at a temperature level particularly advantageous for heating the third component mixture of in particular 80° C. to 100° C., for example about 90° C. and the extent of the cooling to a temperature level of 25° C. to 50° C., for example about 40° C., corresponds largely to the extent of the heating of the third component mixture. The first component mixture too may before its introduction into the scrubber be subjected to a cooling in heat exchange with the third component mixture, so that the cooling power to be effected in the scrubber, and thus the heating of the second component mixture, is reduced.

In the context of the present invention the second component mixture, i.e. the bottoms liquid of the scrubber, comprises in particular 5% to 20% by weight, for example about 11% by weight, of acetic acid and in the remaining proportion at least 80% by weight of water. The second component mixture comprises a remainder proportion of further byproducts of ODH-E such as were previously elucidated.

As mentioned hereinabove the second component mixture, i.e. the bottoms liquid of the scrubber, is generated in particular at a temperature level of 80° C. to 100° C. and the second component mixture is thus formed at this temperature level. The first and/or the second proportion of the second component mixture are, as likewise mentioned hereinabove, cooled to a temperature level of 25° C. to 50° C., in particular to a temperature level of for example about 40° C.

The solvent extraction in the context of the present invention is advantageously performed using at least one solvent having a boiling point in the range from 40° C. to 100° C. (at ambient pressure). Overall it may be noted that the higher the temperature level of the second component mixture and the lower the pressure of the third component mixture the more effective are the measures proposed in the context of the present invention. Furthermore, the lower the evaporation temperature of the solvent employed in the solvent extraction the more advantageous is the present invention because this ensures that the temperature level at which the third component mixture evaporates is correspondingly low. It is particularly advantageous in the context of the present invention to employ methyl tert-butyl ether (MTBE).

These advantages are achievable in particular when the scrubbing operation, optionally the solvent extraction and the distillation and also the heating of the third component mixture are performed at a pressure level substantially equal to atmospheric pressure, for example a pressure level of 0.9 to 1.2 bar (abs.) in particular about atmospheric pressure. In the solvent extraction, for example as a result of hydrostatics alone, the pressure level may also be markedly higher and depend in particular on the column height and the densities of the employed fluids.

As already addressed briefly at the outset in the context of the present invention the distillation affords a gaseous fourth component mixture containing at least the organic solvent(s) from the solvent extraction and small amounts of water and also acetic acid. The water may advantageously be separated predominantly in a simple liquid-liquid separator. The thus obtained water phase is advantageously at least partly supplied to a stripping operation together with the acetic acid-depleted water phase from the extraction. In the stripping operation the organic solvent(s) and other light byproducts are at least partly driven out of the water phase using a stripping gas.

Particularly suitable as stripping gas in the context of the present invention is low pressure steam at a temperature level of 120° C. to 220° C. The stripping operation too is therefore a separation step having high energy requirements, particularly when the low pressure steam must be provided specifically for the process. A heating of the acetic acid-depleted water phase from the extraction and/or the water phase from the fourth component mixture may therefore also be advantageous because this increases the volatility of the solvent and facilitates the stripping. This heating in particular is also effected by heat exchanger with the first and/or the second proportion of the second component mixture.

The present invention also provides a plant for producing ethylene comprising at least one reactor adapted for partly catalytically converting ethane in a reaction input by oxidative dehydrogenation in the presence of oxygen to obtain a gaseous first component mixture containing at least ethane, ethylene, acetic acid and water. The plant features at least one scrubbing column adapted for subjecting at least a portion of the gaseous first component mixture to a scrubbing operation with a first scrubbing liquid to obtain a liquid second component mixture containing water and acetic acid. Also provided are means adapted for using a first proportion of the second component mixture for forming the scrubbing liquid and at least one extraction column adapted for subjecting a second proportion of the second component mixture to a solvent extraction to obtain a liquid third component mixture containing at least one organic solvent and acetic acid. Finally provided are means adapted for heating at least a portion of the liquid third component mixture and at least one distillation column adapted for at least partly subjecting the heated liquid third component mixture or the heated proportion thereof to a distillation to obtain a liquid containing predominantly or exclusively acetic acid.

For features and advantages of a corresponding plant reference is made explicitly to the features and advantages elucidated with reference to the process proposed according to the invention. Advantageously, such a plant is adapted for performing such a process.

The invention is more particularly elucidated hereinafter with reference to the appended drawing illustrating a preferred embodiment of the invention.

BRIEF DESCRIPTION OF THE DRAWING

FIG. 1 shows a process according to one embodiment of the invention.

DETAILED DESCRIPTION OF THE DRAWING

FIG. 1 shows a process according to a particularly preferred embodiment of the present invention in the form of a schematic process flow diagram given the collective label 100.

In the process 100 a process gas stream a from an ODH-E 1, shown here only in a highly schematic form, is supplied to a lower region of a scrubber 2, into whose upper region a material stream b described hereinbelow is applied. In this way at least the predominant portion of the water present in the process gas stream a and the acetic acid present in the process gas stream a is separated in the bottom of the scrubber 2. Obtainable in this way from the top of the scrubber 2 is a process gas stream c freed of at least a predominant portion of the water present and the acetic acid present.

Withdrawn from the bottom of the scrubber 2 is an aqueous acetic acid solution in the form of a material stream d. As previously mentioned hereinabove the acetic acid solution has a content of about 11% by weight of acetic acid for example and a temperature level of for example about 90° C. The material stream c is cooled in three heat exchangers 3, 4 and 5, of which the heat exchangers 3 and 4 are operated with the material streams I and u elucidated hereinbelow and the heat exchanger 5 is operated for example with cooling water. Downstream of the heat exchanger 5 a portion of the material stream d is diverted in the form of the material stream b previously mentioned hereinabove. This affords a corresponding circuit. In other words a portion of the aqueous acetic acid solution withdrawn from the bottom is applied in the upper portion of the scrubber 2 after a corresponding cooling.

A residual stream remaining after the diverting of the material stream b, now referred to as e for clarity, is introduced at a temperature level of for example about 40° C. into an upper region of an extraction column 6 which is operated at an atmospheric pressure level and a temperature level corresponding to ambient temperature. The extraction column 6 is supplied in a lower region with a solvent stream f which is formed using a solvent stream g formed as is elucidated hereinbelow and a solvent stream h withdrawn from a solvent tank 7. The solvent tank 7 may in turn be supplied with a solvent stream i. The solvent may be expelled from the solvent tank 7 using an inert gas stream k. The solvent may be in particular MTBE, and the inert gas in particular nitrogen.

Withdrawable in this way from an upper region of the extraction column 6 is a material stream I containing essentially acetic acid and the solvent employed. Said stream is passed using a pump 8 through the previously mentioned heat exchanger 3, heated therein and thus pre-evaporated or even fully evaporated and introduced into a distillation column 9 which is likewise operated at an atmospheric pressure level. As already mentioned hereinabove the heat exchanger 3 need not necessarily exist as a separate apparatus for the material stream I but rather may also be integrated in the form of an intermediate reboiler in the distillation 9.

A bottoms evaporator 10 of the distillation column 9 may in particular be operated using low pressure steam. Through the heating of the material stream I it is possible, as mentioned previously, in the context of the present invention to achieve an energy saving via a lower heat requirement in the bottoms evaporator 10. A desired cooling of the material stream d may be effected simultaneously as a result. Generated in the bottom of the distillation column 9 is substantially pure acetic acid (glacial acetic acid) which may be withdrawn in the form of a material stream m, pumped by means of a pump 11 through a heat exchanger 12 operated with cooling water and for example discharged as a product at the plant limits.

The tops product of the distillation column 9 comprises predominantly the solvent employed in the extraction column 6 and small amounts of water and acetic acid. This is withdrawn in the form of a material stream n, passed through a heat exchanger 13 operated with cooling water and together with a material stream x more particularly elucidated hereinbelow introduced into a separator 14. Withdrawn from said separator using a pump 15 is a material stream o containing predominantly solvent and small amounts of acetic acid, a first proportion of which is recycled in the form of a material stream p as reflux onto the distillation column 9 and a second proportion of which is used in the form of a material stream q for forming the previously mentioned solvent stream g. To this end the material stream q is combined with a further solvent stream r conveyed by means of a pump 16 from a further solvent tank 17. The further solvent tank 17 is supplied with solvent in the form of a material stream s. Further withdrawn from the separator 14 using a pump 18 is a material stream t which is predominantly aqueous but also contains residual proportions of the employed solvent and is used as elucidated hereinbelow.

From a lower region of the extraction column 6 using a pump 19 a material stream u containing predominantly water but also residual proportions of the employed solvent is withdrawn, passed through the previously mentioned heat exchanger 4, combined with the likewise previously mentioned material stream t and introduced into a stripping column 20. Low-pressure steam is introduced into the stripping column 20 as stripping gas in the form of a material stream v. The stripping column 20 has a lower column section 21 and an upper column section 22, wherein the lower column section 21 and the upper column section 22 are separated from one another by an overflow tray 23, for example a chimney neck tray. The lower column section 21 and the upper column section 22 may be dimensioned differently as required.

The top of the upper column section 22 of the stripping column 20 may for example be cooled using a cooling water stream w. Formed in this way on the overflow tray 23 is a liquid containing predominantly the remaining solvent present in the material streams u and t which may be withdrawn in the form of the previously mentioned material stream x. A tops gas remaining in the top of the upper column section 22 of the stripping column 20 comprises in particular light hydrocarbons likewise scrubbed into the liquid phase in the quench column 2. These may be flared or sent for another use for example.

Withdrawn from the bottom of the lower column section 21 of the stripping column 20 by means of a pump 24 and for example discharged at the plant limits is a material stream z containing predominantly water.

The invention claimed is:

1. A process (100) for producing ethylene and/or acetic acid, comprising:
    partly catalytically converting ethane in a reaction input by oxidative dehydrogenation (1) in presence of oxygen to obtain a gaseous first component mixture containing at least ethane, ethylene, acetic acid and water, and
    subjecting at least a portion of the gaseous first component mixture to a scrubbing operation with a scrubbing liquid to obtain a liquid second component mixture containing water and acetic acid and a process gas stream containing ethane and ethylene,
    using a first proportion of the liquid second component mixture as the scrubbing liquid,
    subjecting a second proportion of the liquid second component mixture to a solvent extraction to obtain a liquid third component mixture containing at least one organic solvent and acetic acid, and
    heating and subjecting at least a portion of the liquid third component mixture to a distillation to obtain a liquid containing predominantly or exclusively acetic acid,
    wherein the heating of the at least the portion of the liquid third component mixture subjected to the distillation is performed at least partly in heat exchange with the gaseous first component mixture and/or with the first and/or with the second proportion of the liquid second component mixture.

2. The process (100) according to claim 1, in which the heating of the at least the portion of the liquid third component mixture subjected to the distillation is performed at a temperature range of 40° C. to 120° C.

3. The process (100) according to claim 2, in which the liquid second component mixture contains 5% to 20% by weight of acetic acid and at least 80% by weight of water.

4. The process (100) according to claim 2, in which the liquid second component mixture is formed at a temperature range of 80° C. to 100° C. and the first and/or the second proportion of the liquid second component mixture are cooled to a temperature range of 25° C. to 50° C.

5. The process (100) according to claim 2, in which the solvent extraction is performed using at least one solvent having a boiling point in a range from 40° C. to 100° C. (at ambient pressure).

6. The process (100) according to claim 2, in which in the solvent extraction a further component mixture containing predominantly the water from the liquid second component mixture and a proportion of the solvents(s) is formed, wherein the further component mixture is heated in heat exchange with the gaseous first component mixture and/or with the first and/or with the second proportion of the liquid second component mixture.

7. The process (100) according to claim 1, in which the liquid second component mixture contains 5% to 20% by weight of acetic acid and at least 80% by weight of water.

8. The process (100) according to claim 7, in which the liquid second component mixture is formed at a temperature level range of 80° C. to 100° C. and the first and/or the second proportion of the liquid second component mixture are cooled to a temperature loyal range of 25° C. to 50° C.

9. The process (100) according to claim 7, in which the solvent extraction is performed using at least one solvent having a boiling point in a range from 40° C. to 100° C. (at ambient pressure).

10. The process (100) according to claim 1, in which the liquid second component mixture is formed at a temperature range of 80° C. to 100° C. and the first and/or the second proportion of the liquid second component mixture are cooled to a temperature range of 25° C. to 50° C.

11. The process (100) according to claim 10, in which the solvent extraction is performed using at least one solvent having a boiling point in a range from 40° C. to 100° C. (at ambient pressure).

12. The process (100) according to claim 1, in which the solvent extraction is performed using at least one solvent having a boiling point in a range from 40° C. to 100° C. at ambient pressure.

13. The process (100) according to claim 12, in which the at least one solvent comprises methyl tert-butyl ether.

14. The process (100) according to claim 1, in which at least the scrubbing operation and the distillation are performed at a pressure range of 0.9 to 1.1 bara.

15. The process (100) according to claim 1, in which in the solvent extraction a further component mixture containing predominantly the water from the liquid second component mixture and a proportion of the solvents(s) is formed, wherein the further component mixture is heated in heat exchange with the gaseous first component mixture and/or with the first and/or with the second proportion of the liquid second component mixture.

16. The process according to claim 15, in which the further component mixture contains 1 to 10 percent by mass, of the solvent(s).

17. The process (100) according to claim 15, in which the further component mixture is supplied to a stripping operation.

18. The process (100) according to claim 1, in which the distillation is performed with heating by means of steam.

19. A plant producing ethylene and/or acetic acid, comprising:
    at least one reactor adapted for partly catalytically converting ethane in a reaction input by oxidative dehydrogenation (1) in presence of oxygen to obtain a gaseous first component mixture containing at least ethane, ethylene, acetic acid and water, at least one scrubbing column adapted for subjecting at least a portion of the gaseous first component mixture to a scrubbing operation with a scrubbing liquid to obtain a liquid second component mixture containing water and acetic acid and a process gas stream containing ethane and ethylene, a conduit adapted for sending a first proportion of the liquid second component mixture to the at least one scrubbing column as the scrubbing liquid, at least one extraction column adapted for subjecting a second proportion of the liquid second component mixture to a solvent extraction to obtain a liquid third component mixture containing at least one organic solvent and acetic acid, at least one heat exchanger adapted for heating at least a portion of the liquid third component mixture at least partly in heat exchange with the gaseous first component mixture and/or with the first and/or with the second proportion of the liquid second component mixture, and at least one distillation column adapted for at least partly subjecting the heated portion of the liquid third component mixture to a distillation to obtain a liquid containing predominantly or exclusively acetic acid.

* * * * *